United States Patent [19]

Teraji et al.

[11] 4,332,800

[45] Jun. 1, 1982

[54] CEPHEM COMPOUNDS

[75] Inventors: Tsutomu Teraji, Osaka; Kazuo Sakane, Amagasaki; Jiro Goto, Suita, all of Japan

[73] Assignee: Fujisawa Pharmaceutical Co., Ltd., Osaka, Japan

[21] Appl. No.: 214,785

[22] Filed: Dec. 9, 1980

Related U.S. Application Data

[63] Continuation-in-part of Ser. No. 180,295, Aug. 22, 1980.

[30] Foreign Application Priority Data

Oct. 12, 1979 [GB] United Kingdom ................. 7935538
Oct. 1, 1980 [ZA] South Africa ....................... 80/6068

[51] Int. Cl.$^3$ ............................................ C07D 501/36
[52] U.S. Cl. ....................................... 424/246; 544/25; 544/27
[58] Field of Search ...................... 544/26, 27, 25, 21, 544/16, 30; 424/246

[56] References Cited

U.S. PATENT DOCUMENTS

| 4,079,178 | 3/1978 | Cook et al. | 544/26 |
| 4,093,803 | 6/1978 | Cook et al. | 544/27 |
| 4,098,888 | 7/1978 | Ochiai et al. | 424/246 |
| 4,166,115 | 8/1979 | Takaya et al. | 424/246 |
| 4,254,260 | 3/1981 | Takaya et al. | 544/27 |
| 4,258,041 | 3/1981 | O'Callaghan et al. | 544/27 |
| 4,263,291 | 4/1981 | Takaya et al. | 544/27 |

FOREIGN PATENT DOCUMENTS 2745246  4/1978  Fed. Rep. of Germany .

Primary Examiner—Nicholas S. Rizzo
Attorney, Agent, or Firm—Oblon, Fisher, Spivak, McClelland & Maier

[57] ABSTRACT

This invention relates to novel cephem compounds of high antimicrobial activity and more particularly to 7-aminothiadiazole alkoxyimino acetamido cephem derivatives with substitution in the 3-position of the cephem nucleus of carbamoyl-pyridiniomethyl grouping or methyl-oxo-hydroxy-dihydrotriazinyl thiomethyl grouping.

15 Claims, No Drawings

CEPHEM COMPOUNDS

This application is a continuation-in-part of application Ser. No. pending 180,295, filed Aug. 22, 1980.

The present invention relates to new cephem compounds and pharmaceutically acceptable salts thereof. More particularly, it relates to new cephem compounds and pharmaceutically acceptable salts thereof, which have antimicrobial activities and to processes for preparation thereof, to pharmaceutical composition comprising the same, and to a method of using the same therapeutically in the treatment of infectious diseases in human being and animals.

Accordingly, it is one object of the present invention to provide new cephem compounds and pharmaceutically acceptable salts thereof, which are active against a number of pathogenic microorganisms.

Another object of the present invention is to provide processes for the preparation of new cephem compounds and pharmaceutically acceptable salts thereof. A further object of the present invention is to provide pharmaceutical composition comprising, as active ingredients, said new cephem compounds and pharmaceutically acceptable salts thereof.

Still further object of the present invention is to provide a method for the treatment of infectious diseases caused by pathogenic bacteria in human being and animals.

The object new cephem compounds are novel and can be represented by the following general formula (I).

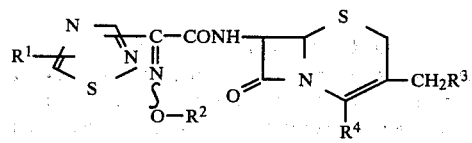

wherein
$R^1$ is amino or protected amino group;
$R^2$ is lower alkyl;
$R^3$ is a group of the formula:

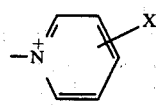

wherein X is hydrogen or carbamoyl and $R^4$ is $-COO^-$; or
$R^3$ is dihydrotriazinylthio substituted with lower alkyl, oxo and hydroxy and
$R^4$ is carboxy or protected carboxy.

According to the present invention, the new cephem compounds (I) can be prepared by various processes which are illustrated in the following scheme.

Process 1

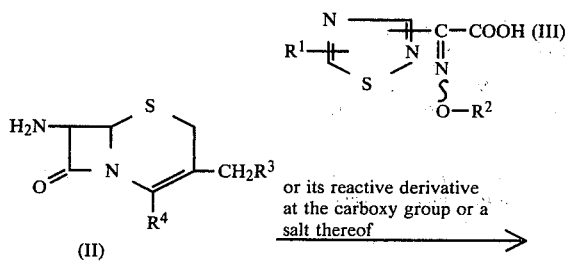

or its reactive derivative at the amino group or a salt thereof

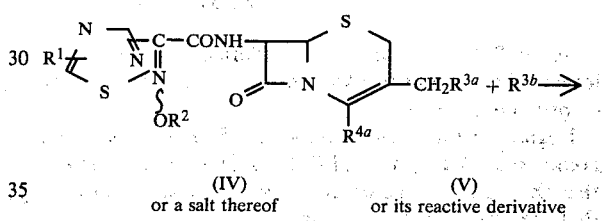

or a salt thereof

Process 2

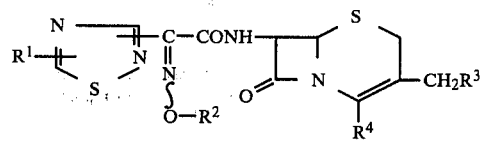

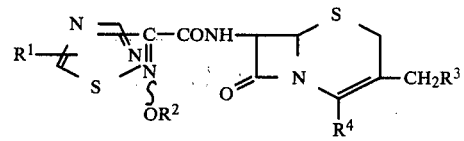

or a salt thereof wherein
$R^1$, $R^2$, $R^3$ and $R^4$ are each as defined above;
$R^{3a}$ is a group which can be substituted with a group of the formula: $R^3$ wherein $R^3$ is as defined above;
$R^{3b}$ is a compound of the formula:

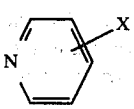

wherein
X is as defined above and
$R^{4a}$ is carboxy; or
$R^{3b}$ is a compound of the formula: $R^{3c}$—H wherein $R^{3c}$ is dihydrotriazinylthio substituted with lower alkyl, oxo and hydroxy and $R^{4a}$ is carboxy or protected carboxy.

Among the starting compounds of the present invention, some of the compounds of the formula (IV) are novel and can be prepared by the following method.

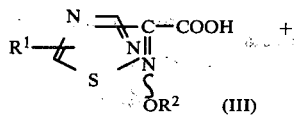

or its reactive derivative at the carboxy group or a salt thereof

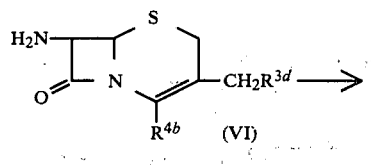

or its reactive derivative at the amino group or a salt thereof

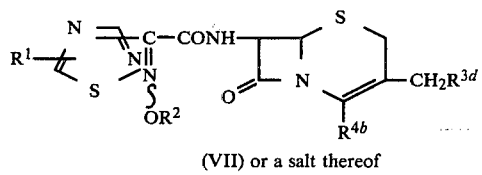

(VII) or a salt thereof wherein $R^1$ and $R^2$ are each as defined above, $R^{3d}$ is lower alkanoyl(lower)alkanoyloxy and $R^{4b}$ is carboxy or protected carboxy.

Regarding the object compound (I) and the starting compounds (III), (IV) and (VII), it is to be understood that they include tautomeric isomers. That is, in case that the group of the formula:

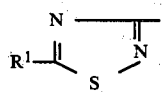

($R^1$ is as defined above) is contained in the molecules of said object and starting compounds, said group of the formula can also be alternatively represented by its tautomeric formula:

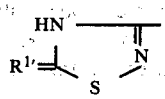

($R^{1'}$ is imino or a protected imino group.) That is, the both of said groups are in the state of equilibrium each other and such tautomerism can be represented by the following equilibrium.

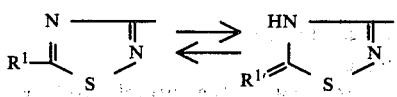

wherein $R^1$ and $R^{1'}$ are each as defined above.

These types of tautomerism between the amino-compound and the corresponding imino-compound as stated above have been well known in the literature, and it is obvious to a person skilled in the arts that both of the tautomeric isomers are easily convertible reciprocally and are included within the same category of the compound per se.

Accordingly, the both of the tautomeric forms of the object compound (I) and the starting compounds (III), (IV) and (VII) are clearly included within the scope of the present invention. In the present specification and claims, the object and starting compounds including the group of such tautomeric isomers are represented by using one of the expressions therefor, that is the formula:

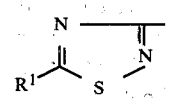

Furthermore, regarding the object compound (I) and the starting compounds (III), (IV) and (VII), it is to be understood that said object and starting compounds include syn isomer, anti isomer and a mixture thereof. For example, with regard to the object compound (I), syn isomer means one geometrical isomer having the partial structure represented by the following formula:

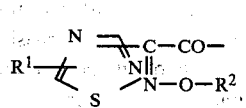

(wherein $R^1$ and $R^2$ are each as defined above) and anti isomer means the other geometrical isomer having the partial structure represented by the following formula:

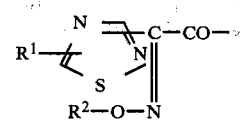

(wherein $R^1$ and $R^2$ are each as defined above).

Regarding the starting compounds (III), (IV) and (VII) as mentioned above, the syn isomer and the anti isomer can also be referred to the same geometrical isomers as illustrated for the compound (I).

Suitable pharmaceutically acceptable salts of the object compounds (I) are conventional non-toxic salt and include a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), an organic acid salt (e.g. acetate, maleate, tartrate, methanesulfonate, benzenesulfonate, formate, toluenesulfonate, etc.), an inorganic acid salt (e.g. hydrochloride, hydrobromide, hydroiodide, sulfate, phosphate, etc.), or a salt with an amino acid (e.g. arginine, aspartic acid, glutamic acid, etc.), and the like.

In the above and subsequent descriptions of the present specification, suitable examples and illustrations of the various definitions which the present invention include within the scope thereof are explained in details as follows.

The term "lower" is intended to mean 1 to 6 carbon atoms, unless otherwise indicated.

Suitable "protected amino" for $R^1$ may include an acylamino or an amino group substituted by a conventional protecting group such as ar(lower)alkyl which may have at least one suitable substituent(s), (e.g. benzyl, trityl, etc.) or the like.

Suitable acyl moiety in the term "acylamino" may include carbamoyl, aliphatic acyl group and acyl group containing an aromatic or heterocyclic ring. And, suitable examples of the said acyl may be lower alkanoyl (e.g. formyl, acetyl, propionyl, butyryl, isobutyryl, valeryl, isovaleryl, oxalyl, succinyl, pivaloyl, etc.); lower alkoxycarbonyl (e.g. methoxycarbonyl, ethoxycarbonyl, propoxycarbonyl, 1-cyclopropylethoxycarbonyl, isopropoxycarbonyl, butoxycarbonyl, tertiarybutoxycarbonyl, pentyloxycarbonyl, hexyloxycarbonyl, etc.); lower alkanesulfonyl (e.g. mesyl, ethanesulfonyl, propanesulfonyl, isopropanesulfonyl, butanesulfonyl, etc.);

arenesulfonyl (e.g. benzenesulfonyl, tosyl, etc.); aroyl (e.g. benzoyl, toluoyl, xyloyl, naphthoyl, phthaloyl, indancarbonyl, etc.); ar(lower)alkanoyl (e.g. phenylacetyl, phenylpropionyl, etc,);

ar(lower)alkoxycarbonyl (e.g. benzyloxycarbonyl, phenethyloxycarbonyl, etc.), and the like.

The acyl moiety as stated above may have at least one suitable substituent(s) such as halogen (chlorine, bromine, fluorine and iodine) or the like.

Suitable "lower alkyl" for $R^2$ is one having 1 to 6 carbon atom(s) and may include methyl, ethyl, propyl, isopropyl, butyl, isobutyl, tert-butyl, pentyl, tert-pentyl, hexyl and the like, and preferably one having 1 to 4 carbon atom(s).

Suitable lower alkyl substituent on dihydrotriazinylthio can be referred to the ones as exemplified above.

Suitable protected carboxy may include esterified carboxy in which said ester may be the ones such as lower alkyl ester (e.g., methyl ester, ethyl ester, propyl ester, isopropyl ester, butyl ester, isobutyl ester, t-butyl ester, pentyl ester, t-pentyl ester, hexyl ester, 1-cyclopropylethyl ester, etc.), wherein lower alkyl moiety may be preferably one having 1 to 4 carbon atom(s); lower alkenyl ester (e.g., vinyl ester, allyl ester, etc.); lower alkynyl ester (e.g., ethynyl ester, propynyl ester, etc.); mono(or di or tri)-halo(lower)alkyl ester (e.g., 2-iodoethyl ester, 2,2,2-trichloroethyl ester, etc.);

lower alkanoyloxy(lower)alkyl ester (e.g., acetoxymethyl ester, propionyloxymethyl ester, butyryloxymethyl ester, valeryloxymethyl ester, pivaloyloxymethyl ester, hexanoyloxymethyl ester, 2-acetoxyethyl ester, 2-propionyloxyethyl ester, etc.);

lower alkanesulfonyl(lower)alkyl ester (e.g., mesylmethyl ester, 2-mesylethyl ester etc.);

ar(lower)alkyl ester, for example, phenyl(lower)alkyl ester which may be substituted with one or more suitable substituent(s) (e.g., benzyl ester, 4-methoxybenzyl ester, 4-nitrobenzyl ester, phenethyl ester, trityl ester, diphenylmethyl ester, bis(methoxyphenyl)methyl ester, 3,4-dimethoxybenzyl ester, 4-hydroxy-3,5-ditertiarybutylbenzyl ester, etc.);

aryl ester which may have one or more suitable substituent(s) (e.g., phenyl ester, tolyl ester, tertiarybutylphenyl ester, xylyl ester, mesityl ester, cumenyl ester, etc.), and the like.

Suitable $R^{3a}$ may include acyloxy, halogen (e.g., chlorine, bromine, iodine or fluorine), azido and the like, wherein acyl moiety in the "acyloxy" can be referred to the ones as exemplified above.

Suitable lower alkanoyl(lower)alkanoyloxy may include acetoacetoxy, propionylacetoxy, acetopropionyloxy and the like.

Preferred embodiment of the present invention is shown as follows.

Preferable example of $R^1$ is amino;
$R^2$ is lower alkyl;
$R^3$ is a group of the formula:

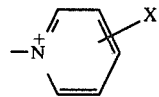

wherein X is hydrogen or carbamoyl and $R^4$ is —COO$^-$; or $R^3$ is 2-lower alkyl-5-oxo-6-hydroxy-2,5-dihydro-1,2,4-triazinylthio and $R^4$ is carboxy.

The processes for preparing the object compounds of the present invention are explained in details in the following.

Process 1

The object compound (I) or a salt thereof can be prepared by reacting the compound (II) or its reactive derivative at the amino group or a salt thereof with the compound (III) or its reactive derivative at the carboxy group or a salt thereof.

Suitable reactive derivative at the amino group of the compound (II) may include Schiff's base type imino or its tautomeric enamine type isomer formed by the reaction of the compound (II) with a carbonyl compound such as aldehyde, ketone or the like; a silyl derivative formed by the reaction of the compound (II) with a silyl compound such as bis(trimethylsilyl)acetamide or the like; a derivative formed by reaction of the compound (II) with phosphorus trichloride or phosgene, and the like.

Suitable salt of the compounds (II) and (III) may include an acid addition salt such as an organic acid salt (e.g., acetate, maleate, tartrate, benzenesulfonate, toluenesulfonate, etc.) or an inorganic acid salt (e.g., hydrochloride, hydrobromide, sulfate, phosphate, etc.); a metal salt (e.g., sodium salt, potassium salt, calcium salt, magnesium salt, etc.); ammonium salt; an organic amine salt (e.g., triethylamine salt, dicyclohexylamine salt, etc.), and the like.

Suitable reactive derivative at the carboxy group of the compound (III) may include an acid halide, an acid anhydride, an activated amide, an activated ester, and the like. The suitable example may be an acid chloride, an acid azide; a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc), dialkylphosphorous acid, sulfurous acid, thiosulfuric acid, sulfuric acid, alkylcarbonic acid, aliphatic carboxylic acid (e.g., pivalic acid, pentanoic acid, isopentanoic acid, 2-ethylbutyric acid or trichloroacetic acid, etc.) or aromatic carboxylic acid (e.g. benzoic acid, etc.); a symmetrical acid anhydride; an activated amide with imidazole, 4-substituted imidazole, dimethylpyrazole, triazole or tetrazole; or an activated ester (e.g., cyanomethyl ester, methoxymethyl ester, dimethyliminomethyl [(CH$_3$)$_2$N$^+$=CH—] ester, vinyl ester, propargyl ester, p-nitrophenyl ester, 2,4-dinitrophenyl ester, trichlorophenyl ester, pentachlorophenyl ester, mesyl phenyl ester, phenylazophenyl ester, phenyl thioester, p-nitrophenyl thioester p-cresyl thioester, carboxymethyl thioester, pyranyl ester, pyridyl ester, piperidyl ester, 8-quinolyl thioester, etc.), or an ester with a N-hydroxy compound (e.g., N,N-dimethylhydroxylamine, 1-hydroxy-2-(1H)-pyridone, N-hydroxysuccinimide, N-hydroxyphthalimide, 1-hydroxy-6-chloro-1H-benzotriazole, etc.), and the like. These reactive derivatives can optionally be selected from them according to the kind of the compound (III) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvents which do not adversely influence the reaction. These conventional solvents may also be used in a mixture with water.

When the compound (III) is used in free acid form or its salt form in the reaction, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N-carbonylbis-(2-methyl imidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus pentachloride; phosphorus oxychloride; phosphorus trichloride; thionyl chloride; oxalyl chloride; triphenylphosphine; 2-ethyl-7-hydroxybenzisoxazolium salt; 2-ethyl-5-(m-sulfophenyl)isoxazolium hydroxide intra-molecular salt; 1-(p-chlorobenzenesulfonyloxy)-6-chloro-1H-benzotriazole; so-called Vilsmeier reagent prepared by the reaction of dimethylformamide with thionyl chloride, phosgene, phosphorus oxychloride, etc.; or the like.

The reaction may also be carried out in the presence of an inorganic or organic base such as an alkali metal bicarbonate, tri(lower)alkylamine, pyridine, N-(lower)alkylmorphorine, N,N-di(lower)alkylbenzylamine, or the like. The reaction temperature is not critical, and the reaction is usually carried out under cooling or at ambient temperature.

In the present reaction, a syn isomer of the object compound (I) can be obtained preferably by reacting the compound (II) with the corresponding syn isomer of the starting compound (III).

Process 2

The object compound (I) or a salt thereof can be prepared by reacting the compound (IV) of a salt thereof with the compound (V) or its reactive derivative.

Suitable salt of the compound (IV) can be referred to the ones exemplified for the compound (II).

Suitable reactive derivative of the compound (V) may include a metal salt such as an alkali metal salt (e.g., sodium salt, potassium salt, etc.) or the like.

The present reaction may be carried out in a solvent such as water, phosphate buffer, acetone, chloroform, nitrobenzene, methylene chloride, ethylene chloride, formamide, dimethylformamide, methanol, ethanol, ether, tetrahydrofuran, dimethylsulfoxide, or any other organic solvent which does not adversely affect the reaction, preferably in ones having strong polarities. Among the solvents, hydrophilic solvents may be used in a mixture with water. The reaction is preferably carried out in around neutral medium. When the compound (IV) and the compound (V) is used in a free form, the reaction is preferably conducted in the presence of a base, for example, inorganic base such as alkali metal hydroxide, alkali metal carbonate, alkali metal bicarbonate, organic base such as trialkylamine, and the like. The reaction temperature is not critical, and the reaction is usually carried out at ambient temperature, under warming or under slightly heating. The present reaction is preferably carried out in the presence of alkali metal halide (e.g., sodium iodide, potassium iodide, etc), alkali metal thiocyanate (e.g., sodium thiocyanate, potassium thiocyanate, etc) etc.

The preparation for preparing the starting compounds (VII) is explained below.

Preparation

The compound (VII) or a salt thereof can be prepared by reacting the compound (III) or its reactive derivative at the carboxy group or a salt thereof with the compound (VI) or its reactive derivative at the amino group or a salt thereof.

Suitable reactive derivative and salt for the compound (VI) can be referred to the ones as exemplified for the compound (II).

The present reaction can be carried out in substantially the same manner as that of Process 1.

In the aforementioned reactions and/or the post-treating of the reactions of the present invention, the aforementioned geometrical isomer and/or tautomeric isomer may occasionally be transformed into the other geometrical isomer and/or tautomeric isomer and such cases are to be also included in the scope of the present invention.

In case that the object compound (I) has a free carboxy group and/or a free amino group, it may be transformed into its pharmaceutically acceptable salt as aforementioned by a conventional method.

The object compound (I) can be purified into crystal forms by conventional methods.

The object compound (I) of the present invention exhibits high antimicrobial activity and inhibits the growth of a number of microorganisms including pathogenic Gram-positive and Gram-negative bacteria.

For therapeutic administration, the cephalosporin compounds according to the present invention are used in the form of pharmaceutical preparation which contain said compounds in admixture with a pharmaceutically acceptable carriers such as an organic or inorganic solid or liquid excipient suitable for oral, parenteral or external administration. The pharmaceutical preparations may be in solid form such as capsule, tablet, dragee, ointment or suppository, or in liquid form such as solution, suspension, or emulsion. If desired, there may be included in the above preparations auxiliary substances, stabilizing agents, wetting or emulsifying agents, buffers and other commonly used additives.

While the dosage of the compounds may vary from and also depend upon the age and condition of the patient, an average single dose of about 50 mg., 100 mg., 250 mg., and 500 mg. of the compounds according to the present invention has proved to be effective for treating of infectious diseases caused by a number of pathogenic bacteria. In general amounts, daily dose between 1 mg/body and about 1000 mg/body or even more may be administered.

Now in order to show the utility of the object compounds (I), test data on anti-microbial activity of a representative compound of the present invention are shown below.

Test Method

One loopful of an overnight culture of each test strain in Trypticase-soy broth ($10^8$ viable cells per ml.) was streaked on heart infusion agar (HI-agar) containing graded concentrations of antibiotics, and the minimal inhibitory concentration (MIC) was expressed in terms of μg/ml after incubation at 37° C. for 20 hours.

Test compound (1) 7-[2-Ethoxyimino-2-(5-amino-1,2,4-thiadiazol-3-yl)acetamido]-3-(1-pyridiniomethyl)-3-cephem-4-carboxylate (syn isomer)
(2) 7-[2-Propoxyimino-2-(5-amino-1,2,4-thiadiazol-3-yl)acetamido]-3-(1-pyridiniomethyl)-3-cephem-4-carboxylate (syn isomer)
(3) 7-[2-Ethoxyimino-2-(5-amino-1,2,4-thiadiazol-3-yl)acetamido]-3-(4-carbamoyl-1-pyridiniomethyl)-3-cephem-4-carboxylate (syn isomer)

Test Results

| | Test Compound MIC(μg/ml) | | |
|---|---|---|---|
| Test Bacteria | (1) | (2) | (3) |
| B. subtilis ATCC 6633 | 0.78 | 0.39 | 0.78 |
| Ps. aeruginosa 2 | 3.13 | 12.50 | 25.0 |
| S. marcescens 35 | 1.56 | 3.13 | 3.13 |

The following Examples and Preparation are given for the purpose of illustrating the present invention.

EXAMPLE 1

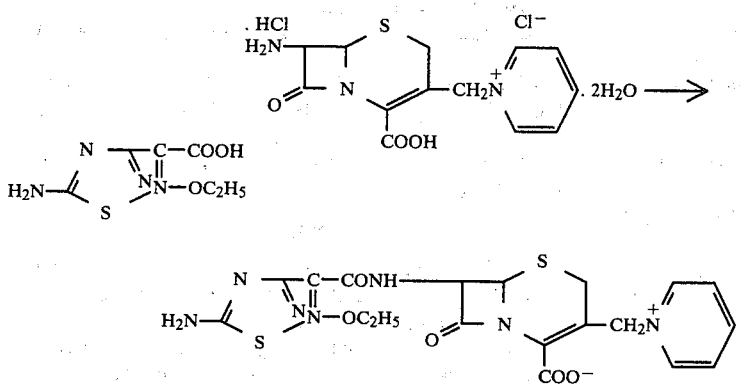

To a cold solution of phosphorus pentachloride (2.64 g) in methylene chloride (25 ml) was added 2-ethoxyimino-2-(5-amino-1,2,4-thiadiazol-3-yl)acetic acid (syn isomer) (2.48 g) at −20° C. and the mixture was stirred for 35 minutes at −20° to −14° C. To the mixture was added cold diisopropyl ether (75 ml) below −10° C. under stirring, which was continued until the mixture was warmed to ambient temperature. The resulting precipitates were collected by filtration, washed with diisopropyl ether and then kept in a desiccator for several minutes. On the other hand, a mixture of 1-[(7-amino-4-carboxy-3-cephem-3-yl)methyl]pyridinium chloride hydrochloride dihydrate (3.27 g) and trimethylsilylacetamide (16 g) in methylene chloride (50 ml) was warmed at 35° C. to make a solution, which was cooled to −20° C. To the cold solution were added the precipitates prepared above and the mixture was stirred for 25 minutes at −18° to −12° C. and for an additional 20 minutes at −12° to −3° C. A solution of sodium bicarbonate (4 g) in water (30 ml) was added to the reaction mixture and the aqueous layer was separated out, adjusted to pH 1 with 6 N hydrochloric acid, washed with ethyl acetate and then readjusted to pH 4 with an aqueous solution of sodium bicarbonate. The aqueous solution was passed through a column packed with alumina (16 g) and then subjected to column chromatography on a non-ionic adsorption resin Diaion HP-20 (trademark: prepared by Mitsubishi Chemical Industries) (100 ml). After the column was washed with water, the elution was carried out with 20% aqueous methanol. The eluates containing an object compound were collected, evaporated to remove methanol under reduced pressure and lyophilized to give white powder of 7-[2-ethoxyimino-2-(5-amino-1,2,4-thiadiazol-3-yl)acetamido]-3-(1-pyridiniomethyl)-3-cephem-4-carboxylate (syn isomer) (2.39 g), mp. 155° to 165° C. (dec.).

IR (Nujol): 3400–3150, 1770, 1660, 1610, 1530 cm$^{-1}$.
NMR (DMSO-d$_6$, δ): 1.21 (3H, t, J=7 Hz), 2.9–3.7 (2H, m), 4.12 (2H, q, J=7 Hz), 5.05 (1H, d, J=5 Hz), 5.19, 5.68 (2H, ABq, J=14 Hz), 5.7 (1H, m), 8.1 (4H, m), 8.6 (1H, m), 9.4 (3H, m).

EXAMPLE 2

The following compounds were obtained according to a similar manner to that of Example 1.
(1) 7-[2-Propoxyimino-2-(5-amino-1,2,4-thiadiazol-3-yl)acetamido]-3-(1-pyridiniomethyl)-3-cephem-4-carboxylate (syn isomer), mp. 230° to 240° C. (dec.).
IR (Nujol): 3400–3200, 1770, 1670–1600, 1530 cm$^{-1}$.
NMR (DMSO-d$_6$, δ): 0.85 (3H, t, J=7 Hz), 1.6 (2H, m), 3.06, 3.55 (2H, ABq, J=18 Hz), 4.04 (2H, t, J=6 Hz), 5.06 (1H, d, J=5 Hz), 5.18, 5.70 (2H, ABq, J=14 Hz), 5.74 (1H, dd, J=5 and 8 Hz), 8.2 (4H, m), 8.6 (1H, m), 9.5 (3H, m).
(2) 7-[2-Methoxyimino-2-(5-amino-1,2,4-thiadiazol-3-yl)acetamido]-3-(1-pyridiniomethyl)-3-cephem-4-carboxylate (syn isomer), mp. 250° to 260° C. (dec.).
IR (Nujol): 3400–3100, 1770, 1650, 1610, 1520 cm$^{-1}$.
NMR (DMSO-d$_6$, δ): 3.07, 3.57 (2H, ABq, J=18 Hz), 3.86 (3H, s), 5.06 (1H, d, J=5 Hz), 5.19, 5.69 (2H, ABq, J=14 Hz), 5.73 (1H, dd, J=5, 8 Hz), 8.0–8.3 (4H, m), 8.4–8.7 (1H, m), 9.3–9.6 (3H, m).
(3) 7-[2-Isopropoxyimino-2-(5-amino-1,2,4-thiadiazol-3-yl)acetamido]-3-(1-pyridiniomethyl)-3-cephem-4-carboxylate (syn isomer), mp. 160° to 165° C. (dec.).
IR (Nujol): 3270, 3180, 1770, 1660, 1610, 1525 cm$^{-1}$
NMR (DMSO-d$_6$+D$_2$O, δ): 1.22 (6H, d, J=6 Hz), 3.15, 3.57 (2H, ABq, J=18 Hz), 4.17–4.60 (1H, m), 5.12

(1H, d, J=5 Hz), 5.33, 5.70 (2H, ABq, J=14 Hz), 5.78 (1H, d, J=5 Hz), 8.0-8.4 (2H, m), 8.47-8.83 (1H, m), 9.33-9.67 (2H, m).

(4) 7-[2-Ethoxyimino-2-(5-amino-1,2,4-thiadiazol-3-yl)acetamido]-3-(4-carbamoyl-1-pyridiniomethyl)-3-cephem-4-carboxylate (syn isomer), mp 160° to 165° C. (dec.).

IR (Nujol): 3300, 3200, 1780, 1680, 1620, 1570, 1530 cm$^{-1}$.

(5) 7-[2-Methoxyimino-2-(5-amino-1,2,4-thiadiazol-3-yl)acetamido]-3-(4-carbamoyl-1-pyridiniomethyl)-3-cephem-4-carboxylate (syn isomer), mp 165° to 170° C. (dec.).

IR (Nujol): 3350, 3200, 1780, 1690, 1610, 1570, 1530 cm$^{-1}$.

(6) 7-[2-Propoxyimino-2-(5-amino-1,2,4-thiadiazol-3-yl)acetamido]-3-(4-carbamoyl-1-pyridiniomethyl)-3-cephem-4-carboxylate (syn isomer), mp 170° to 175° C. (dec.).

IR (Nujol): 3350, 3200, 1780, 1690, 1610, 1570, 1530 cm$^{-1}$.

(7) 7-[2-Isopropoxyimino-2-(5-amino-1,2,4-thiadiazol-3-yl)acetamido]-3-(4-carbamoyl-1-pyridiniomethyl)-3-cephem-4-carboxylate (syn isomer), mp 155° to 160° C. (dec.).

IR (Nujol): 3350, 3220, 1780, 1680, 1615, 1570, 1530 cm$^{-1}$.

(8) Disodium 7-[2-methoxyimino-2-(5-amino-1,2,4-thiadiazol-3-yl)acetamido]-3-(2-methyl-5-oxo-6-oxido-2,5-dihydro-1,2,4-triazin-3-yl)thiomethyl-3-cephem-4-carboxylate (syn isomer), mp 220° to 225° C. (dec.).

IR (Nujol): 3400-3150, 1760, 1660, 1640-1560, 1520, 1040 cm$^{-1}$.

(9) Disodium 7-[2-ethoxyimino-2-(5-amino-1,2,4-thiadiazol-3-yl)acetamido]-3-(2-methyl-5-oxo-6-oxido-2,5-dihydro-1,2,4-triazin-3-yl)thiomethyl-3-cephem-4-carboxylate (syn isomer), mp 255° to 265° C. (dec.).

IR (Nujol): 3400-3150, 1760, 1660, 1600, 1500, 1400, 1030 cm$^{-1}$.

(10) 7-[2-Isopropoxyimino-2-(5-amino-1,2,4-thiadiazol-3-yl)acetamido]-3-(2-methyl-5-oxo-6-hydroxy-2,5-dihydro-1,2,4-triazin-3-yl)thiomethyl-3-cephem-4-carboxylic acid (syn isomer), mp 160° to 167° C. (dec.).

IR (Nujol): 3400, 3280, 3180, 1780, 1770, 1630, 1515, 1410, 1240, 1009 cm$^{-1}$.

NMR (DMSO-d$_6$+D$_2$O, δ): 1.27 (6H, d, J=6 Hz), 3.62 (3H, s), 3.5-3.9 (2H, m), 4.13, 4.41 (2H, ABq, J=14 Hz), 4.40 (1H, t, J=6 Hz), 5.17 (1H, d, J=5 Hz), 5.83 (1H, d, J=5 Hz).

EXAMPLE 3

To a solution of sodium iodide (10 g) and pyridine (1.28 g) in formamide (8 ml) was added sodium 7-[2-ethoxyimino-2-(5-amino-1,2,4-thiadiazol-3-yl)acetamido]-cephalosporanate (syn isomer) (4.0 g) at 75° C. under stirring, which was continued for 1.5 hours at 80° to 85° C. The mixture was cooled to ambient temperature and poured into ethanol (100 ml). A resulting precipitate was collected by filtration and an additional one was obtained from the filtrate by an addition of diisopropyl ether (100 ml). These precipitates were dissolved in water (50 ml) and the solution was adjusted to pH 3 with 6 N hydrochloric acid and washed with ethyl acetate. The aqueous solution was subjected to column chromatography on a non-ionic adsorption resin Diaion HP-20 (Trademark, prepared by Mitsubishi Chemical Industries) (160 ml). After the column was washed with water, the elution was carried out with 30% aqueous methanol. The eluates containing an object compound were collected, evaporated to remove methanol under reduced pressure and lyophilized to give white powder of 7-[2-ethoxyimino-2-(5-amino-1,2,4-thiadiazol-3-yl)acetamido]-3-(1-pyridiniomethyl)-3-cephem-4-carboxylate (syn isomer) (1.52 g), mp. 155° to 165° C. (dec.).

IR (Nujol): 3400-3150, 1770, 1660, 1610, 1530 cm$^{-1}$.

EXAMPLE 4

A mixture of 7-[2-ethoxyimino-2-(5-amino-1,2,4-thiadiazol-3-yl)acetamido]-3-acetoacetoxymethyl-3-cephem-4-carboxylic acid (syn isomer) (14.2 g), sodium bicarbonate (2.33 g), potassium iodide (140 g) and 4-carbamoyl-pyridine (5.08 g) in water (140 ml) was stirred for 2.75 hours at 55° C. After cooling, ethyl acetate (100 ml) and 6 N hydrochloric acid were added thereto under stirring to adjust the pH of the mixture to 2. The aqueous layer was separated out, washed with ethyl acetate and concentrated under reduced pressure. An insoluble substance was filtered off and the filtrate was subjected to column chromatography on a non ionic adsorption resin, Diaion HP20 (300 ml). After the column was washed with water (500 ml), the elution was carried out with 30% aqueous methanol. The eluates containing an object compound were collected, evaporated to remove methanol under reduced pressure and lyophilized to give 7-[2-ethoxyimino-2-(5-amino-1,2,4-thiadiazol-3-yl)acetamido]-3-(4-carbamoyl-1-pyridiniomethyl)-3-cephem-4-carboxylate (syn isomer) (4.7 g), mp 160° to 165° C. (dec.).

IR (Nujol): 3300, 3200, 1780, 1680, 1620, 1570, 1530 cm$^{-1}$.

NMR (DMSO-d$_6$+D$_2$O, δ): 1.33 (3H, t, J=7 Hz), 3.33, 3.67, (2H, ABq, J=18 Hz), 4.35 (2H, q, J=7 Hz), 5.30 (1H, d, J=4 Hz), 5.47, 5.67 (2H, ABq, J=14 Hz), 5.90 (1H, d, J=4 Hz), 8.40 (2H, d, J=7 Hz), 9.17 (2H, d, J=7 Hz).

EXAMPLE 5

The following compounds were obtained according to similar manners to those of Examples 3 and 4.

(1) 7-[2-Methoxyimino-2-(5-amino-1,2,4-thiadiazol-3-yl)acetamido]-3-(4-carbamoyl-1-pyridiniomethyl)-3-cephem-4-carboxylate (syn isomer), mp 165° to 170° C. (dec.).

IR (Nujol): 3350, 3200, 1780, 1690, 1610, 1570, 1530 cm$^{-1}$.

NMR (D$_2$O, δ): 3.33, 3.67 (2H, ABq, J=18 Hz), 4.07 (3H, s), 5.30 (1H, d, J=4 Hz), 5.47, 5.67 (2H, ABq, J=14 Hz), 5.90 (1H, d, J=4 Hz), 8.40 (2H, d, J=7 Hz), 9.17 (2H, d, J=7 Hz).

(2) 7-[2-Propoxyimino-2-(5-amino-1,2,4-thiadiazol-3-yl)acetamido]-3-(4-carbamoyl-1-pyridiniomethyl)-3-cephem-4-carboxylate (syn isomer), mp 170° to 175° C. (dec.).

IR (Nujol): 3350, 3200, 1780, 1690, 1610, 1570, 1530 cm$^{-1}$.

NMR (D$_2$O, δ): 0.95 (3H, t, J=7 Hz), 1.5-2.0 (2H, m), 3.33, 3.68 (2H, ABq, J=17 Hz), 4.28 (2H, t, J=7 Hz), 5.33 (1H, d, J=4 Hz), 5.47, 5.70 (2H, ABq, J=14 Hz), 5.92 (1H, d, J=4 Hz), 8.42 (2H, d, J=7 Hz), 9.17 (2H, d, J=7 Hz).

(3) 7-[2-Isopropoxyimino-2-(5-amino-1,2,4-thiadiazol-3-yl)acetamido]-3-(4-carbamoyl-1-pyridiniomethyl)-3- cephem-4-carboxylate (syn isomer), mp 155° to 160° C. (dec.).

IR (Nujol): 3350, 3220, 1780, 1680, 1615 1570, 1530 cm$^{-1}$.

NMR (DMSO-d$_6$+D$_2$O, δ): 1.22 (6H, d, J=6 Hz), 3.17, 3.48 (2H, ABq, J=18 Hz), 4.1–4.6 (1H, m), 5.03 (1H, d, J=5 Hz), 5.25, 5.63 (2H, ABq, J=14 Hz), 5.70 (1H, d, J=5 Hz), 8.40 (2H, d, J=6 Hz), 9.45 (2H, d, J=6 Hz).

(4) Disodium 7-[2-methoxyimino-2-(5-amino-1,2,4-thiadiazol-3-yl)acetamido]-3-(2-methyl-5-oxo-6-oxido-2,5-dihydro-1,2,4-triazin-3-yl)thiomethyl-3-cephem-4-carboxylate (syn isomer), mp 220° to 225° C. (dec.).

IR (Nujol): 3400–3150, 1760, 1660, 1640–1560, 1520, 1040 cm$^{-1}$.

NMR (D$_2$O, δ): 3.64 (3H, s), 3.48, 3.78 (2H, ABq, J=18 Hz), 4.08 (3H, s), 4.00–4.56 (2H, m), 5.20 (1H, d, J=5 Hz), 5.82 (1H, d, J=5 Hz).

(5) Disodium 7-[2-ethoxyimino-2-(5-amino-1,2,4-thiadiazol-3-yl)acetamido]-3-(2-methyl-5-oxo-6-oxido-2,5-dihydro-1,2,4-triazin-3-yl)thiomethyl-3-cephem-4-carboxylate (syn isomer), mp 255° to 265° C. (dec.).

IR (Nujol): 3400–3150, 1760, 1660, 1600, 1500, 1400, 1030 cm$^{-1}$.

NMR (D$_2$O, δ): 1.35 (3H, t, J=7 Hz), 3.42, 3.80 (2H, ABq, J=18 Hz), 3.65 (3H, s), 4.07, 4.43 (2H, ABq, J=13 Hz), 4.38 (2H, q, J=7 Hz), 5.22 (1H, d, J=5 Hz), 5.83 (1H, d, J=5 Hz).

(6) 7-[2-Isopropoxyimino-2-(5-amino-1,2,4-thiadiazol-3-yl)acetamido]-3-(2-methyl-5-oxo-6-hydroxy-2,5-dihydro-1,2,4-triazin-3-yl)thiomethyl-3-cephem-4-carboxylic acid (syn isomer), mp 160° to 167° C. (dec.).

IR (Nujol): 3400, 3280, 3180, 1780, 1770, 1630, 1515, 1410, 1240, 1009 cm$^{-1}$.

EXAMPLE 6

(Purification of the object compound)

A powder (0.2 g) of 7-[2-ethoxyimino-2-(5-amino-1,2,4-thiadiazol-3-yl)acetamido]-3-(1-pyridiniomethyl)-3-cephem-4-carboxylate (syn isomer) was dissolved in water (0.8 ml) and dropped acetone (1.6 ml) thereto under stirring at ambient temperature. After few minutes, the stirring was stopped and the solution was stood for 1.5 hours at ambient temperature to crystallize. The resulting colorless needles were filtered, washed with 90% aqueous acetone (1 ml×2) and acetone (1 ml×3) and dried for 9 hours under reduced pressure to give colorless needles of 7-[2-ethoxyimino-2-(5-amino-1,2,4-thiadiazol-3-yl)acetamido]-3-(1-pyridiniomethyl)-3-cephem-4-carboxylate acetone adduct monohydrate (syn isomer) (120 mg), mp >155° C. (dec.).

IR (Nujol): 3430–3120, 1760, 1700, 1680, 1615, 1530 cm$^{-1}$.

NMR (D$_2$O, δ): 1.32 (3H, t, J=7 Hz), 2.26 (6H, s), 3.20 and 3.72 (2H, ABq, J=17 Hz), 4.37 (2H, q, J=7 Hz), 5.30 (1H, d, J=5 Hz), 5.35 and 5.66 (2H, ABq, J=14 Hz), 5.91 (1H, d, J=5 Hz), 8.12 (2H, m), 8.61 (1H, m), 8.98 (2H, m).

| Analysis for C$_{19}$H$_{19}$N$_7$O$_5$S$_2$ . C$_3$H$_6$O . H$_2$O | | | |
|---|---|---|---|
| | C | H | N | H$_2$O |
| Calcd: | 46.72 | 4.81 | 17.34 | 3.18 |
| Found: | 46.79 | 4.79 | 16.72 | 3.24 |

EXAMPLE 7

(Purification of the object compound)

2-Ethoxyimino-2-(5-amino-1,2,4-thiadiazol-3-yl)acetic acid (syn isomer) (11.4 g) and 1-[(7-amino-4-carboxy-3-cephem-3-yl)methyl]pyridinium chloride hydrochloride dihydrate (24 g) were reacted according to a similar manner to that of Example 1.

To the reaction mixture was added water (300 ml) and the mixture was adjusted to pH 1.5 with an aqueous solution of sodium hydroxide and subjected to column chromatography on a non-ionic adsorption resin Diaion HP-20 (960 ml). After the column was washed with water (3.6 l) and eluted with 30% aqueous methanol. (1.26 l). The eluates were collected and concentrated under reduced pressure to a volume of 110 ml. The solution was subjected to column chromatography on acidic alumina (120 g) and eluted with water. The eluates containing 7-[2-ethoxyimino-2-(5-amino-1,2,4-thiadiazol-3-yl)acetamido]-3-(1-pyridiniomethyl)-3-cephem-4-carboxylate (syn isomer) (310 ml) were collected and acetone (1.1 l) was added thereto with stirring at ambient temperature for 5 minutes. The mixture was stirred for 1.5 hours under ice-cooling and precipitates were collected by filtration, in turn washed with 90% aqueous solution of acetone (80 ml) and acetone (240 ml), and then dried under reduced pressure to give crystals (20 g) of 7-[2-ethoxyimino-2-(5-amino-1,2,4-thiadiazol-3-yl)acetamido]-3-(1-pyridiniomethyl)-3-cephem-4-carboxylate acetone adduct (syn isomer). The crystals were dissolved in water (40 ml) and the solution was passed through a column packed with acidic alumina (40 g). The elution was carried out with water and the eluates (140 ml) were collected. To the solution was added acetone (300 ml) at ambient temperature under stirring, which was stopped in a minute. The mixture was stood for 20 minutes at ambient temperature and for 1.5 hours in a refrigerator. The resulting colorless needles were filtered, washed with 90% aqueous acetone (25 ml×3) and acetone (25 ml×3) and dried for 3.5 hours under reduced pressure to give pure colorless needles of 7-[2-ethoxyimino-2-(5-amino-1,2,4-thiadiazol-3-yl)acetamido]-3-(1-pyridiniomethyl)-3-cephem-4-carboxylate acetone adduct (syn isomer) (14.3 g), mp >157° C.

EXAMPLE 8

(Purification of the object compound)

A solution of 7-[2-ethoxyimino-2-(5-amino-1,2,4-thiadiazol-3-yl)acetamido]-3-(1-pyridiniomethyl)-3-cephem-4-carboxylate acetone adduct (syn isomer) (1.0 g) in water (1 ml) was stood on for 5 days in a freezer at −20° C. A mixture of ice and precipitates was stood on at ambient temperature until the ice was melted. The resulting precipitates were collected by filtration, washed with water (0.3 ml) and dried in vacuo to give 7-[2-ethoxyimino-2-(5-amino-1,2,4-thiadiazol-3-yl)acetamido]-3-(1-pyridiniomethyl)-3-cephem-4-carboxylate (syn isomer) (0.52 g) as colorless needles, mp 165° to 170° C. (dec.).

IR (Nujol): 3450–3200, 3070, 1765, 1665, 1630, 1600, 1530, 1485 cm$^{-1}$.

NMR (D$_2$O, δ): 1.32 (3H, t, J=7 Hz), 3.20 and 3.72 (2H, ABq, J=17 Hz), 4.33 (2H, q, J=7 Hz), 5.27 (1H, d, J=5 Hz), 5.34 and 5.65 (2H, ABq, J=14 Hz), 5.89 (1H, d, J=5 Hz), 8.10 (2H, m), 8.60 (1H, m), 8.97 (2H, m).

EXAMPLE 9

(Purification of the object compound)

To a solution of 7-[2-ethoxyimino-2-(5-amino-1,2,4-thiadiazol-3-yl)acetamido]-3-(1-pyridiniomethyl)-3-cephem-4-carboxylate acetone adduct (syn isomer) (40 g) in water (50 ml) was added a small amount of colorless needles of 7-[2-ethoxyimino-2-(5-amino-1,2,4-thiadiazol-3-yl)acetamido]-3-(1-pyridiniomethyl)-3-cephem-4-carboxylate (syn isomer) and the mixture was stirred for one hour in an ice bath. The resulting precipitates were collected by filtration, washed with cold water (33 ml) and dried in vacuo for 10 hours to give 7-[2-ethoxyimino-2-(5-amino-1,2,4-thiadiazol-3-yl)acetamido]-3-(1-pyridiniomethyl)-3-cephem-4-carboxylate dihydrate (syn isomer) (24.7 g), as colorless needles, mp 170° to 175° C. (dec.).

Water content (K.F. method) Calcd: 6.72%, Found: 6.20%.

EXAMPLE 10

(Purification of the object compound)

A powder of 7-[2-methoxyimino-2-(5-amino-1,2,4-thiadiazol-3-yl)acetamido]-3-(1-pyridiniomethyl)-3-cephem-4-carboxylate (syn isomer) (7.7 g) was dissolved in water (15.4 ml) and the solution was allowed to stand overnight in a refrigerator. Precipitates were filtered, in turn washed with 80% isopropyl alcohol (5 ml) and isopropyl alcohol (5 ml), air-dried for 1 hour and then dried in vacuo for 2 hours to give colorless needles of 7-[2-methoxyimino-2-(5-amino-1,2,4-thiadiazol-3-yl)acetamido]-3-(1-pyridiniomethyl)-3-cephem-4-carboxylate (syn isomer) (4.2 g), mp 165° to 170° C. (dec.).

IR (Nujol): 3300, 3200, 1765, 1670, 1630, 1605, 1550–1520 cm$^{-1}$.

NMR (D$_2$O, δ): 3.24, 3.70 (2H, ABq, J=18 Hz), 4.06 (3H, s), 5.28 (1H, d, J=5 Hz), 5.36, 5.60 (2H, ABq, J=14 Hz), 5.87 (1H, d, J=5 Hz), 8.06 (2H, m), 8.54 (1H, m), 8.95 (2H, m).

Preparation

The following compounds were obtained according to a similar manner to that of Example 1.

(1) Sodium 7-[2-ethoxyimino-2-(5-amino-1,2,4-thiadiazol-3-yl)acetamido]-3-acetoacetoxymethyl-3-cephem-4-carboxylate (syn isomer), mp 175° to 180° C. (dec.).

IR (Nujol): 3450, 3300, 3100, 1790, 1720, 1670, 1640, 1610, 1550 cm$^{-1}$.

NMR (D$_2$O, δ): 1.38 (3H, t, J=6 Hz), 2.34 (3H, s), 3.44, 3.66 (2H, ABq, J=18 Hz), 4.40 (2H, q, J=6 Hz), 5.05, 5.86 (2H, ABq, J=12 Hz), 5.26 (1H, d, J=4 Hz), 5.90 (1H, d, J=4 Hz).

(2) 7-[2-Methoxyimino-2-(5-amino-1,2,4-thiadiazol-3-yl)acetamido]-3-acetoacetoxymethyl-3-cephem-4-carboxylic acid (syn isomer), mp 120° to 125° C. (dec.).

IR (Nujol): 3350, 3250, 1780, 1710, 1680, 1630, 1530 cm$^{-1}$.

NMR (D$_2$O+NaHCO$_3$, δ): 2.32 (3H, s), 3.40, 3.62 (2H, ABq, J=18 Hz), 4.10 (3H, s), 4.84, 5.04 (2H, ABq, J=14 Hz), 5.22 (1H, d, J=4 Hz), 5.86 (1H, d, J=4 Hz).

(3) 7-[Propoxyimino-2-(5-amino-1,2,4-thiadiazol-3-yl)acetamido]-3-acetoacetoxymethyl-3-cephem-4-carboxylic acid (syn isomer), mp 125° to 130° C. (dec.).

IR (Nujol): 3350, 3250, 1780, 1710, 1680, 1620, 1530 cm$^{-1}$.

NMR (D$_2$O+NaHCO$_3$, δ): 0.94 (3H, t, J=6 Hz), 1.5–1.9 (2H, m), 2.30 (3H, s), 3.40, 3.62 (2H, ABq, J=18 Hz), 4.26 (2H, t, J=6 Hz), 4.84, 5.04 (2H, ABq, J=12 Hz), 5.22 (1H, d, J=4 Hz), 5.86 (1H, d, J=4 Hz).

(4) 7-[2-Isopropoxyimino-2-(5-amino-1,2,4-thiadiazol-3-yl)acetamido]-3-acetoacetoxymethyl-3-cephem-4-carboxylic acid (syn isomer), mp 95° to 100° C. (dec.).

IR (Nujol): 3400, 3300, 3200, 1775, 1740, 1710, 1670, 1620, 1525 cm$^{-1}$.

NMR (DMSO-d$_6$, δ): 1.28 (6H, d, J=6 Hz), 2.18 (3H, s), 3.48, 3.60 (2H, ABq, J=18 Hz), 3.62 (2H, s), 4.24–4.54 (1H, m), 4.78, 5.02 (2H, ABq, J=13 Hz), 5.14 (1H, d, J=5 Hz), 5.80 (1H, dd, J=5 and 8 Hz), 8.06 (2H, broad s), 9.44 (1H, d, J=8 Hz).

What we claim is:

1. Cephem compounds comprising the syn isomer of the formula:

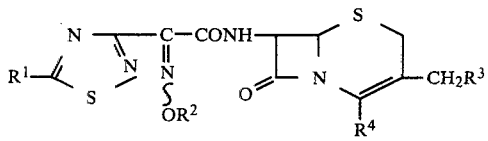

wherein
R$^1$ is amino or a protected amino group,
R$^2$ is lower alkyl of from 1 to 6 carbon atoms,
R$^3$ is a group of the formula

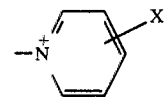

wherein
X is carbamoyl, and
R$^4$ is —COO$^-$, or
R$^3$ is dihydrotriazinylthio substituted with lower alkyl, oxo and hydroxy, and R$^4$ is carboxy or protected carboxy, and pharmaceutically acceptable salts thereof.

2. A compound of claim 1, wherein R$^1$ is amino.

3. A compound of claim 2, wherein R$^3$ is a group of the formula:

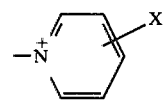

and R$^4$ is —COO$^-$.

4. A compound of claim 1, wherein R$^2$ is methyl, ethyl, propyl or isopropyl.

5. The compound 7-[2-methoxyimino-2-(5-amino-1,2,4-thiadiazol-3-yl)acetamido]-3-(4-carbamoyl-1-pyridiniomethyl)-3-cephem-4-carboxylate (syn isomer).

6. The compound 7-[2-ethoxyimino-2-(5-amino-1,2,4-thiadiazol-3-yl)acetamido]-3-(4-carbamoyl-1-pyridiniomethyl)-3-cephem-4-carboxylate (syn isomer).

7. The compound 7-[2-propoxyimino-2-(5-amino-1,2,4-thiadiazol-3-yl)acetamido]-3-(4-carbamoyl-1-pyridiniomethyl)-3-cephem-4-carboxylate (syn isomer).

8. The compound 7-[2-isopropoxyimino-2-(5-amino-1,2,4-thiadiazol-3-yl)acetamido]-3-(4-carbamoyl-1-pyridiniomethyl)-3-cephem-4-carboxylate (syn isomer).

9. A compound of claim 2, wherein $R^3$ is dihydrotriazinylthio substituted with lower alkyl, oxo and hydroxy and $R^4$ is carboxy.

10. A compound of claim 9, wherein $R^3$ is 2-lower alkyl-5-oxo-6-hydroxy-2,5-dihydro-1,2,4-triazin-3-ylthio.

11. A compound of claim 10, wherein $R^2$ is methyl, ethyl or isopropyl and $R^3$ is 2-methyl-5-oxo-6-hydroxy-2,5-dihydro-1,2,4-triazin-3-ylthio.

12. The compound 7-[2-methoxyimino-2-(5-amino-1,2,4-thiadiazol-3-yl)acetamido]-3-(2-methyl-5-oxo-6-hydroxy-2,5-dihydro-1,2,4-triazin-3-yl)thiomethyl-3-cephem-4-carboxylic acid (syn isomer) or its disodium salt.

13. The compound 7-[2-ethoxyimino-2-(5-amino-1,2,4-thiadiazol-3-yl)acetamido]-3-(2-methyl-5-oxo-6-hydroxy-2,5-dihydro-1,2,4-triazin-3-yl)thiomethyl-3-cephem-4-carboxylic acid (syn isomer) or its disodium salt.

14. The compound 7-[2-isopropoxyimino-2-(5-amino-1,2,4-thiadiazol-3-yl)acetamido]-3-(2-methyl-5-oxo-6-hydroxy-2,5-dihydro-1,2,4-triazin-3-yl)thiomethyl-3-cephem-4-carboxylic acid (syn isomer).

15. An antibacterial composition comprising an effective amount of a compound of claim 1 in association with a pharmaceutically acceptable, substantially non-toxic carrier or excipient.

* * * * *

UNITED STATES PATENT AND TRADEMARK OFFICE
CERTIFICATE OF CORRECTION

PATENT NO. : 4,332,800
DATED : June 1, 1980
INVENTOR(S) : TERAJI ET AL

It is certified that error appears in the above—identified patent and that said Letters Patent is hereby corrected as shown below:

In column 16, line 58, "1" should read: --3--.

Signed and Sealed this

Fourteenth Day of September 1982

[SEAL]

Attest:

Attesting Officer

GERALD J. MOSSINGHOFF

Commissioner of Patents and Trademarks